United States Patent
Bryant et al.

(10) Patent No.: US 10,610,502 B1
(45) Date of Patent: Apr. 7, 2020

(54) ORAL BACLOFEN SOLUTIONS

(71) Applicant: Metacel Pharmaceuticals, LLC, Athens, GA (US)

(72) Inventors: Thomas Jeffrey Bryant, Athens, GA (US); H. Greg Thomas, Athens, GA (US)

(73) Assignee: Metacel Pharmaceuticals, LLC, Athens, GA (US)

( * ) Notice: Subject to any disclaimer, the term of this patent is extended or adjusted under 35 U.S.C. 154(b) by 0 days.

(21) Appl. No.: 16/556,893

(22) Filed: Aug. 30, 2019

(51) Int. Cl.
| | |
|---|---|
| *A61K 9/08* | (2006.01) |
| *A61K 31/195* | (2006.01) |
| *A61K 47/14* | (2017.01) |
| *A61K 47/10* | (2017.01) |
| *A61K 47/26* | (2006.01) |
| *A61K 47/12* | (2006.01) |

(52) U.S. Cl.
CPC .............. *A61K 31/195* (2013.01); *A61K 9/08* (2013.01); *A61K 47/10* (2013.01); *A61K 47/12* (2013.01); *A61K 47/14* (2013.01); *A61K 47/26* (2013.01)

(58) Field of Classification Search
None
See application file for complete search history.

(56) References Cited

U.S. PATENT DOCUMENTS 10,300,015 B2    5/2019    Cohen et al.

OTHER PUBLICATIONS

Lioresal 5 mg/5 ml Oral Solution (baclofen) package insert (Sep. 2014).
Pharnext to Launch New Phase 3 Trial of PXT3003 for CMT1A, Sep. 25, 2019 (https://charcot-marie-toothnews.com/2019/09/05/pharnext-to-launch-new-phase-3-trial-for . . . .
MHRA, Baclofen 5 mg/5 mL oral solution, PL 06464/2354 (Nov. 19, 2008).
MHRA, Baclofen 5 mg/5 mL oral solution, PL 17496/0024 (Aug. 2, 2010).
Lioresal Intrathecal (baclofen injection) package insert (Sep. 30, 2016).

*Primary Examiner* — Jennifer A Berrios
(74) *Attorney, Agent, or Firm* — Blank Rome LLP

(57) ABSTRACT

The present disclosure relates to aqueous oral solutions comprising baclofen. In one embodiment, the aqueous oral solutions comprise a buffer comprising citric acid, a salt of citric acid, or any combination thereof, and are stored at from about 2° C. to about 8° C. The present disclosure also relates to buffer free aqueous oral solutions comprising baclofen. Additionally, the present disclosure relates to an assay for determining the amount of an impurity, 4-(3-carboxymethyl)-3-hydroxy-2,5-dioxopyrrolidin-1-yl)-3-(4-chlorophenyl)butanoic acid, in a baclofen containing solution, and to methods of treatment using such aqueous oral solutions.

2 Claims, No Drawings

ORAL BACLOFEN SOLUTIONS

FIELD OF THE INVENTION

The present invention relates to aqueous oral solutions comprising baclofen. In one embodiment, the aqueous oral solution is stored at from about 2° C. to about 8° C. and comprises baclofen and a buffer comprising citric acid, a salt of citric acid, or any combination thereof. The present invention also relates to buffer free aqueous oral solutions comprising baclofen. Additionally, the present invention relates to an assay for determining the amount of an impurity, such as 4-(3-carboxymethyl)-3-hydroxy-2,5-dioxopyrrolidin-1-yl)-3-(4-chlorophenyl)butanoic acid, in a baclofen containing solution, and to methods of treatment using such aqueous oral solutions.

BACKGROUND OF THE INVENTION

Baclofen is a skeletal muscle relaxant and antispastic agent. Baclofen is a structural analog of the inhibitory neurotransmitter gamma-aminobutyric acid (GABA), and may exert its effects by stimulation of the $GABA_B$ receptor subtype.

Lioresal™ Intrathecal (baclofen injection) has been developed for chronic intrathecal infusion for the management of severe spasticity. Baclofen is commercially available for intrathecal injection (Lioresal™ Intrathecal) as a 0.05 mg/mL solution, a 0.5 mg/mL solution or a 2 mg/mL solution having a pH of 5 to 7 in a formulation containing sodium chloride and water.

An oral baclofen solution was previously approved by the UK Medicines and Healthcare Products Regulatory Agency. The solution contained, among other ingredients, citric acid monohydrate and sodium citrate dihydrate. The instructions for the solution specified that it was not to be refrigerated or frozen.

There is a continuing need for safe and effective oral baclofen solutions.

SUMMARY OF THE INVENTION

The present invention relates to aqueous oral solutions comprising baclofen. In one embodiment, the aqueous oral solution is stored at from about 2° C. to about 8° C. and comprises (i) baclofen, (ii) a buffer comprising citric acid, a salt of citric acid, or any combination thereof, and (iii) optionally one or more preservatives.

The present inventors have surprisingly found that baclofen reacts with citric acid to form the impurity 4-(3-carboxymethyl)-3-hydroxy-2,5-dioxopyrrolidin-1-yl)-3-(4-chlorophenyl)butanoic acid, the structure of which is shown below. When tested by high performance liquid chromatograph (HPLC), this impurity co-elutes with a commonly used preservative, methylparaben.

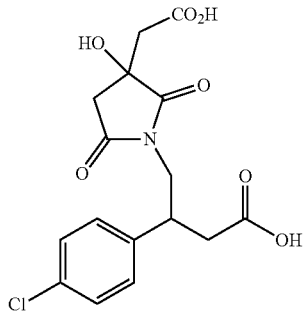 [SMILES: O=C(O)CC(CN1C(=O)CC(O)(CC(=O)O)C1=O)c1ccc(Cl)cc1]

A novel assay has been developed to determine the amount of the impurity 4-(3-carboxymethyl)-3-hydroxy-2,5-dioxopyrrolidin-1-yl)-3-(4-chlorophenyl)butanoic acid in an oral baclofen containing solution. The assay involves performing ion pair chromatography.

The present inventors have also surprisingly found that aqueous oral baclofen may be stored at from about 2° C. to about 8° C. and inhibit the formation of the impurity 4-(3-carboxymethyl)-3-hydroxy-2,5-dioxopyrrolidin-1-yl)-3-(4-chlorophenyl)butanoic acid, while maintaining a functioning solution.

One embodiment of the invention is an aqueous oral solution comprising (i) baclofen, (ii) a buffer comprising citric acid, a salt of citric acid, or any combination thereof, and (iii) optionally one or more preservatives, where the solution is stored at from about 2 to about 8° C. The solution is formulated such that it remains a solution during storage and the baclofen does not precipitate out.

Another embodiment is a buffer-free aqueous oral solution comprising baclofen and one or more preservatives, wherein the solution contains less than about 0.2% of 4-(3-carboxymethyl)-3-hydroxy-2,5-dioxopyrrolidin-1-yl)-3-(4-chlorophenyl)butanoic acid after storage at ambient temperature (e.g., 25° C.) and 60% relative humidity for 3 or 6 months. In another embodiment, buffer-free aqueous oral solution comprising baclofen and one or more preservatives, wherein the solution contains less than about 0.1% or is free of 4-(3-carboxymethyl)-3-hydroxy-2,5-dioxopyrrolidin-1-yl)-3-(4-chlorophenyl)butanoic acid after storage at ambient temperature (e.g., 25° C.) and 60% relative humidity. In one embodiment, the amount of 4-(3-carboxymethyl)-3-hydroxy-2,5-dioxopyrrolidin-1-yl)-3-(4-chlorophenyl)butanoic acid is determined by ion pair chromatography.

In one embodiment of any of the aqueous oral solutions described herein, the solution comprises from about 0.05 to about 0.3% w/v of baclofen, such as from about 0.1 to about 0.3% w/v of baclofen, or from 0.1 to about 0.2% w/v of baclofen.

In one embodiment of any of the aqueous oral solutions described herein, the solution comprises about 0.1% w/v of baclofen. In another embodiment, the solution comprises about 0.2% w/v of baclofen.

In one embodiment of any of the aqueous oral solutions described herein, the one or more preservatives comprise methylparaben, propylparaben, sodium benzoate, sodium methylparaben or a combination thereof. In another embodiment of any of the aqueous oral solutions described herein, the one or more preservatives comprise methylparaben, propylparaben, or a combination thereof. For instance, the oral solution may comprise methylparaben and propylparaben.

In one embodiment of any of the aqueous oral solutions described herein, the solution further comprises glycerin (for instance, as a wetting agent). For instance, the solution may include from about 2 to about 20% w/v, such as from about 5 to about 15% or from about 8 to about 12% w/v, of glycerin.

In one embodiment of any of the aqueous oral solutions containing a buffer described herein, the buffer comprises citric acid, sodium citrate, or a combination thereof. For instance, the oral solution may comprise citric acid and sodium citrate. In another embodiment of any of the aqueous oral solutions containing a buffer described herein, the buffer is a phosphate buffer, such as a sodium phosphate buffer.

In one embodiment of any of the aqueous oral solutions described herein, the solution comprises one or more flavoring agents, such as, e.g., natural grape flavor. Other suitable flavoring agents include but, are not limited to, cotton candy, raspberry, strawberry, lemon-lime, apple and cherry flavors. In one embodiment, the solution comprises from about 0.1 to about 2% w/v flavoring agent (e.g., natural grape flavor), such as about 1.0% w/v flavoring agent.

In one embodiment of any of the aqueous oral solutions described herein, the solution comprises a sweetener, such as sucralose, sucrose, or sodium saccharin. In one embodiment, the solution comprises from about 0.001 to about 1% w/v sweetener. In one preferred embodiment, the solution comprises from about 0.001 to about 1% w/v sucralose, such as about 0.025% w/v sucralose.

In one embodiment of any of the aqueous oral solutions described herein, the pH of the aqueous oral solution ranges from about 4 to about 6 (e.g., from about 4.1 to about 6.0). In another of any of the aqueous oral solutions described herein, the pH of the aqueous oral solution ranges from about 4.3 to about 4.7. For instance, the pH may be 4.3, 4.4, 4.5, 4.6, or 4.7.

In one embodiment of any of the aqueous oral solutions described herein, the solution contains less than about 1%, such as less than about 0.5%, 0.4%, or 0.3% or less than about 0.2% of 4-(3-carboxymethyl)-3-hydroxy-2,5-dioxopyrrolidin-1-yl)-3-(4-chlorophenyl)butanoic acid, after storage, for example, at 2-8° C. for about 3, 6, 9, 12, 18, or 24 months.

In another aspect, the present invention relates to an aqueous oral solution comprising baclofen and one or more preservatives, wherein the solution is free or substantially free (e.g. contains less than about 1% w/v, such as less than about 0.9% w/v, less than about 0.8% w/v, less than about 0.7% w/v, less than about 0.6% w/v, less than about 0.5% w/v, less than about 0.4% w/v, less than about 0.3% w/v, less than about 0.2% w/v, less than about 0.1% w/v, less than about 0.05% w/v, or less than about 0.01% w/v) of 4-(3-carboxymethyl)-3-hydroxy-2,5-dioxopyrrolidin-1-yl)-3-(4-chlorophenyl)butanoic acid, for example, after storage, for example, at 2-8° C. for about 3, 6, 9, 12, 18, or 24 months.

In another aspect, the present invention relates to an aqueous oral solution comprising baclofen and one or more preservatives, wherein the solution contains less than about 0.2% of 4-(3-carboxymethyl)-3-hydroxy-2,5-dioxopyrrolidin-1-yl)-3-(4-chlorophenyl)butanoic acid after storage at 2-8° C. for about 3, 6, 9, 12, 18, or 24 months, such as determined by ion pair chromatography. In one embodiment, the solution contains less than about 0.1% of 4-(3-carboxymethyl)-3-hydroxy-2,5-dioxopyrrolidin-1-yl)-3-(4-chlorophenyl)butanoic acid after storage at 2-8° C. for about 3, 6, 9, 12, 18, or 24 months, such as determined by ion pair chromatography.

Another aspect relates to a method of determining the amount of 4-(3-carboxymethyl)-3-hydroxy-2,5-dioxopyrrolidin-1-yl)-3-(4-chlorophenyl)butanoic acid present in an aqueous oral solution comprising baclofen or a batch of such an aqueous oral solution. The method comprises determining the amount of 4-(3-carboxymethyl)-3-hydroxy-2,5-dioxopyrrolidin-1-yl)-3-(4-chlorophenyl)butanoic acid in the oral solution or a sample of the batch of oral solution by ion pair chromatography.

Yet another embodiment is a method of dispensing to a patient an aqueous oral solution comprising (i) baclofen, (ii) a buffer comprising citric acid, a salt of citric acid, or any combination thereof, and (iii) optionally one or more preservatives. The method comprises (i) storing the solution at from about 2 to about 8° C., and (ii) dispensing the solution to a patient.

Yet another embodiment is a method of determining the amount of 4-(3-carboxymethyl)-3-hydroxy-2,5-dioxopyrrolidin-1-yl)-3-(4-chlorophenyl)butanoic acid in an aqueous oral solution comprising baclofen and a buffer comprising citric acid, a salt of citric acid, or any combination thereof by subjecting the oral solution to ion pair chromatography.

Yet another aspect is a method of relaxing muscles or treating spasticity (e.g., due to spinal cord injury or multiple sclerosis) in a subject in need thereof by administering an oral solution of baclofen as described herein.

DETAILED DESCRIPTION OF THE INVENTION

Definitions

The term "subject" or "patient" encompasses mammals and non-mammals. Examples of mammals include, but are not limited to, any member of the mammalian class: humans, non-human primates such as chimpanzees, and other apes and monkey species; farm animals such as cattle, horses, sheep, goats, and swine; domestic animals such as rabbits, dogs, and cats; and laboratory animals including rodents, such as rats, mice and guinea pigs. Examples of non-mammals include, but are not limited to, birds, fish and the like. In one preferred embodiment, the mammal is a human.

The terms "treat," "treating" or "treatment," as used herein, include alleviating, abating or ameliorating a disease, disorder or condition symptoms, preventing additional symptoms, ameliorating or preventing the underlying causes of symptoms, inhibiting the disease, disorder or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition either prophylactically and/or therapeutically.

As used herein, the term "flavoring agent" is intended to mean a compound used to impart a pleasant flavor and often odor to a pharmaceutical preparation. Exemplary flavoring agents include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavoring agents include vanilla, citrus oil, including lemon, orange, grape (e.g., natural grape), lime and grapefruit, and fruit essences, including apple, pear, peach, strawberry, raspberry, cherry, plum, pineapple, apricot and so forth. In one embodiment, the flavoring agent is natural grape flavor. The amount of flavoring agent may depend on a number of factors, including the organoleptic effect desired. Preferred flavoring agents include grape and cherry flavors and citrus flavors such as orange.

Unless specified otherwise, "storage" of the oral solution (or being "stored") refers to storage in a polyethylene terephthalate container with a polypropylene cap. The container may also be made of any other suitable material such as polypropylene or high density polyethylene (HDPE).

Buffered Oral Solutions

One embodiment of the invention is an aqueous oral solution comprising (i) baclofen, (ii) a buffer comprising citric acid, a salt of citric acid, or any combination thereof, and (iii) optionally one or more preservatives. The solution is preferably stored at from about 2 to about 8° C. (such as when stored in a pharmacy or by a distributor).

In one embodiment, the solution comprises from about 0.05 to about 0.3% w/v of baclofen, such as from about 0.1 to about 0.3% w/v of baclofen, or from 0.1 to about 0.2% w/v of baclofen. For example, the solution may comprise about 0.1% or about 0.2% w/v of baclofen.

The concentration of baclofen in the solution may be about 1 mg/mL. In another embodiment, the solution contains about 2 mg/mL of baclofen.

In one embodiment, the one or more preservatives comprise methylparaben, propylparaben, or a combination thereof. For instance, the oral solution may comprise methylparaben and propylparaben.

Preferably, the solution includes an effective amount of preservatives (such as methylparaben, propylparaben, sodium benzoate, sodium methylparaben, or a combination thereof) to inhibit microbial contamination of the solution. In one embodiment, the solution includes from about 0.01 to about 4% (such as from about 0.05 to about 1% or from about 0.05 to about 0.5%) of preservatives, such as methylparaben, propylparaben, or a combination thereof. In another embodiment, the solution includes from about 0.1 to about 0.2% of preservatives, such as methylparaben, propylparaben, or a combination thereof.

In one embodiment, the solution further comprises glycerin (for instance, as a wetting agent). For instance, the solution may include from about 2 to about 20% w/v, such as from about 5 to about 15% or from about 8 to about 12% w/v, of glycerin.

In one embodiment, the buffer comprises citric acid, sodium citrate, or a combination thereof. For instance, the oral solution may comprise citric acid and sodium citrate. In another embodiment, the buffer is a phosphate buffer, such as a sodium phosphate buffer (e.g., a mixture of monobasic sodium phosphate and dibasic sodium phosphate).

In one embodiment, the solution comprises one or more flavoring agents, such as, e.g., natural grape flavor. Other suitable flavoring agents include but, are not limited to, cotton candy, raspberry, strawberry, lemon-lime, apple and cherry flavors. The flavoring agent may be, for example, natural grape flavor. In one embodiment, the solution comprises from about 0.1 to about 2% w/v of flavoring agent (e.g., natural grape flavor), such as about 1.0% w/v of flavoring agent.

In one embodiment, the solution comprises a sweetener, such as sucralose, sucrose, or sodium saccharin. In another embodiment, the solution comprises from about 0.001 to about 1% w/v sweetener. In one preferred embodiment, the solution comprises from about 0.001 to about 1% w/v sucralose, such as about 0.025% w/v sucralose.

In one embodiment, the pH of the aqueous oral solution ranges from about 4 to about 6. In another embodiment, the pH of the aqueous oral solution ranges from about 4.3 to about 4.7. For instance, the pH may be 4.3, 4.4, 4.5, 4.6, or 4.7.

In one embodiment, the solution contains less than about 1%, such as less than about 0.5%, 0.4%, or 0.3% or less than about 0.2% of 4-(3-carboxymethyl)-3-hydroxy-2,5-dioxopyrrolidin-1-yl)-3-(4-chlorophenyl)butanoic acid, after storage, for example, at 2-8° C. for about 3, 6, 9, 12, 18, or 24 months.

In one preferred embodiment, the oral solution is free or substantially free (e.g. contains less than about 1% w/v, such as less than about 0.9% w/v, less than about 0.8% w/v, less than about 0.7% w/v, less than about 0.6% w/v, less than about 0.5% w/v, less than about 0.4% w/v, less than about 0.3% w/v, less than about 0.2% w/v, less than about 0.1% w/v, less than about 0.05% w/v, or less than about 0.01% w/v) of 4-(3-carboxymethyl)-3-hydroxy-2,5-dioxopyrrolidin-1-yl)-3-(4-chlorophenyl)butanoic acid, for example, after storage, for example, at 2-8° C. for about 3, 6, 9, 12, 18, or 24 months. The amount of 4-(3-carboxymethyl)-3-hydroxy-2,5-dioxopyrrolidin-1-yl)-3-(4-chlorophenyl)butanoic acid can be determined by ion pair chromatography.

In one embodiment, the oral solution is free or substantially free of sorbitol.

Non-Buffered Oral Solutions

One embodiment is a buffer-free aqueous oral solution comprising baclofen and one or more preservatives, wherein the solution contains less than about 0.2% of 4-(3-carboxymethyl)-3-hydroxy-2,5-dioxopyrrolidin-1-yl)-3-(4-chlorophenyl)butanoic acid after storage at ambient temperature (e.g., 25° C.) and 60% relative humidity for 3 or 6 months. In another embodiment, buffer-free aqueous oral solution comprising baclofen and one or more preservatives, wherein the solution contains less than about 0.1% or is free of 4-(3-carboxymethyl)-3-hydroxy-2,5-dioxopyrrolidin-1-yl)-3-(4-chlorophenyl)butanoic acid after storage at ambient temperature (e.g., 25° C.) and 60% relative humidity. In one embodiment, the amount of 4-(3-carboxymethyl)-3-hydroxy-2,5-dioxopyrrolidin-1-yl)-3-(4-chlorophenyl)butanoic acid is determined by ion pair chromatography.

In one embodiment, the oral solution is free or substantially free of sorbitol.

In one embodiment, the buffer-free aqueous oral solution comprises:
  (i) baclofen (for example, in a concentration of about 1 mg/mL or about 2 mg/mL);
  (ii) methylparaben, propylparaben, or a combination thereof;
  (iii) sucralose;
  (iv) a flavoring agent; and
  (v) glycerin.

In one embodiment, the solution comprises from about 0.05 to about 0.3% w/v of baclofen, such as from about 0.1 to about 0.3% w/v of baclofen, or from 0.1 to about 0.2% w/v of baclofen. For instance, the solution may comprise about 0.1% w/v or about 0.2% w/v of baclofen.

Preferably, the solution includes an effective amount of preservatives (such as methylparaben, propylparaben, sodium benzoate, sodium methylparaben, or a combination thereof) to inhibit microbial contamination of the solution. In one embodiment, the solution includes from about 0.01 to about 4% (such as from about 0.05 to about 1% or from about 0.05 to about 0.5%) of preservatives, such as methylparaben, propylparaben, or a combination thereof. In another embodiment, the solution includes from about 0.1 to about 0.2% of preservatives, such as methylparaben, propylparaben, or a combination thereof.

The flavoring agent may be, for example, natural grape flavor. In one embodiment, the solution comprises from about 0.1 to about 2% w/v of flavoring agent (e.g., natural grape flavor), such as about 1.0% w/v of flavoring agent.

In one embodiment, the solution comprises a sweetener, such as sucralose. In one embodiment, the solution comprises from about 0.001 to about 1% w/v sucralose, such as about 0.025% w/v sucralose.

In one embodiment, the pH of the aqueous oral solution ranges from about 4 to about 6. In another embodiment, the pH of the aqueous oral solution ranges from about 4.3 to about 4.7. For instance, the pH may be 4.3, 4.4, 4.5, 4.6, or 4.7.

In another embodiment, the buffer-free aqueous oral solution comprises:
(i) about 0.10% w/v baclofen;
(ii) about 0.15% w/v methylparaben;
(iii) about 0.02% w/v propylparaben;
(iv) about 0.025% w/v sucralose;
(v) about 1.0% w/v flavoring agent (e.g., natural grape flavor); and
(vi) about 10% w/v glycerin.

In yet another embodiment, the buffer-free aqueous oral solution comprises:
(i) about 0.20% w/v baclofen;
(ii) about 0.15% w/v methylparaben;
(iii) about 0.02% w/v propylparaben;
(iv) about 0.025% w/v sucralose;
(v) about 1.0% w/v flavoring agent (e.g., natural grape flavor); and
(vi) about 10% w/v glycerin.

Preparation of Solutions

The baclofen solution can be prepared by, for example, initially heating water and incorporating the preservative (such as parabens) with mixing. The other components, such as a buffer, sweetener, and flavoring agent, are added with mixing. Baclofen may then be added. The baclofen may be wetted (for instance, by mixing with glycerin) prior to being added with the other components. This allows for complete dissolution of the baclofen.

The baclofen solutions described herein may be placed in any suitable container with a suitable cap. The container may be made of polyethylene terephthalate, polypropylene, or high density polyethylene (HDPE). In one embodiment, the container is made of polyethylene terephthalate. The cap may be made of polypropylene.

Method of Dispensing

Another embodiment is a method of dispensing to a patient an aqueous oral solution comprising (i) baclofen, (ii) a buffer comprising citric acid, a salt of citric acid, or any combination thereof, and (iii) optionally one or more preservatives. The method comprises (i) storing the solution at from about 2 to about 8° C., and (ii) dispensing the solution to a patient. The oral solution may be stored and dispensed by, for instance, a pharmacy.

Yet another embodiment is a method of dispensing to a patient a buffer-free aqueous oral solution as described herein. The method comprises (i) storing the solution at from about 2 to about 8° C. or at ambient temperature (e.g., 25° C.), and (ii) dispensing the solution to a patient. The oral solution may be stored and dispensed by, for instance, a pharmacy.

Yet another embodiment is a method of dispensing to a patient a buffer-free aqueous oral solution as described herein. The method comprises (i) storing the solution at ambient temperature (e.g., 25° C.), and (ii) dispensing the solution to a patient. The oral solution may be stored and dispensed by, for instance, a pharmacy.

Assay

Yet another embodiment is a method of determining the amount of 4-(3-carboxymethyl)-3-hydroxy-2,5-dioxopyrrolidin-1-yl)-3-(4-chlorophenyl)butanoic acid in an aqueous oral baclofen solution by subjecting the oral solution to ion pair chromatography. The chromatography can be normal phase liquid chromatography, reverse phase liquid chromatography, or liquid chromatography-mass spectrometry.

The ion pair chromatography may be performed with an ion pair reagent. A suitable ion pair reagent is an alkyl sulfonate, such as sodium 1-pentanesulfonate.

In one embodiment, the mobile phase comprises the ion pair reagent and a buffered acidic solvent. In one embodiment, the buffered acidic solvent comprises methanol, acetic acid, and sodium acetate.

Methods of Treatment

Yet another aspect is a method of relaxing muscles or treating spasticity (e.g., due to spinal cord injury or multiple sclerosis) in a subject in need thereof by administering an oral solution of baclofen as described herein.

One embodiment is a method of relaxing muscles or treating spasticity in a subject in need thereof by orally administering an aqueous oral solution comprising (i) baclofen, (ii) a buffer comprising citric acid, a salt of citric acid, or any combination thereof, and (iii) optionally one or more preservatives, wherein the oral solution contains less than 0.2% 4-(3-carboxymethyl)-3-hydroxy-2,5-dioxopyrrolidin-1-yl)-3-(4-chlorophenyl)butanoic acid as determined by ion pair chromatography.

Another embodiment is a method of relaxing muscles or treating spasticity in a subject in need thereof comprising:
(a) determining the amount of 4-(3-carboxymethyl)-3-hydroxy-2,5-dioxopyrrolidin-1-yl)-3-(4-chlorophenyl)butanoic acid in an aqueous oral solution as described herein (such a solution comprising (i) baclofen, (ii) a buffer comprising citric acid, a salt of citric acid, or any combination thereof, and (iii) optionally one or more preservatives); and
(b) administering an effective amount of the oral solution to the subject when the amount of 4-(3-carboxymethyl)-3-hydroxy-2,5-dioxopyrrolidin-1-yl)-3-(4-chlorophenyl)butanoic acid is below a threshold level.

In one embodiment, the threshold level is 0.2%. In a preferred embodiment, the threshold level is 0.1, 0.05, or 0.02%. These percentages can be determined by the area in the chromatograms from an HPLC.

Yet another embodiment is a method of relaxing muscles or treating spasticity in a subject in need thereof comprising administering to the subject an effective amount of an aqueous oral solution comprising (i) baclofen, (ii) a buffer comprising citric acid, a salt of citric acid, or any combination thereof, and (iii) optionally one or more preservatives, wherein prior to the administration, the amount of 4-(3-carboxymethyl)-3-hydroxy-2,5-dioxopyrrolidin-1-yl)-3-(4-chlorophenyl)butanoic acid in the oral solution is determined to be below a threshold level and the oral solution is stored after the determination, but prior to the administration, at from about 2 to about 8° C.

In one embodiment, the threshold level is 0.2%. In a preferred embodiment, the threshold level is 0.1, 0.05, or 0.02%. These percentages can be determined by the area in the chromatograms from an HPLC.

Yet another embodiment is a method of relaxing muscles or treating spasticity in a subject in need thereof comprising administering an effective amount of an oral baclofen solution to the subject, where (a) the solution comprises (i) baclofen, (ii) a buffer comprising citric acid, a salt of citric acid, or any combination thereof, and (iii) optionally one or more preservatives, and (b) the amount of 4-(3-carboxymethyl)-3-hydroxy-2,5-dioxopyrrolidin-1-yl)-3-(4-chlorophenyl)butanoic acid in the solution was determined as described herein to be below a threshold level. In one embodiment, the threshold level is 0.2%. In a preferred embodiment, the threshold level is 0.1, 0.05, or 0.02%. These percentages can be determined by the area in the chromatograms from an HPLC.

EXAMPLES

Example 1

An oral baclofen solution containing a buffer having the formulation in Table 1 below is prepared as follows. A predetermined amount of water (75% of the total water required) is charged into a jacketed tank capable of heating and large enough to hold the entire batch. The water is heated to 75-80° C. with mixing. Propylparaben is added and mixed for 30-45 minutes. Methylparaben is added and mixed for 15-30 minutes. Upon complete dissolution of the parabens, temperature of the solution is reduced to less than 25° C. Citric acid (mix for 15-30 min.), sucralose (mix for 15-30 min.), sodium citrate dihydrate (mix for 30-60 min,) and grape flavor (mix for 15-30 min.) are added to form a main batch. In a separate vessel large enough to hold the predetermined amount of required glycerin, begin mixing the glycerin and slowly add the baclofen into the vortex of the mixer. When the baclofen is well dispersed in the glycerin and after mixing for 30-60 minutes, transfer the mixture into the main batch with a suitable size pump. The mixture is mixed for an additional 30-60 minutes. The pH is adjusted if necessary. Sufficient water is added and the solution is mixed for 30 minutes.

TABLE 1

| Ingredient | % w/v |
|---|---|
| Purified water USP | 75.000 |
| Propyl paraben NF | 0.020 |
| Methyl paraben NF | 0.150 |
| Citric acid anhydrous USP | 1.200 |
| Sucralose NF | 0.025 |
| Sodium citrate dihydrate USP | 1.850 |
| Natural grape flavor | 1.000 |
| Glycerin 99% USP | 10.000 |
| Baclofen USP | 0.100 |
| Sodium hydroxide NF/Purified water USP/ Hydrochloric acid 10% NF | to achieve pH 4.3 to 4.7 |
| Purified water USP | q.s. |

Example 2

A 1 mg/mL oral baclofen solution without a buffer having the formulation in Table 2 below was prepared by the procedure described in Example 1.

TABLE 2

| Ingredient | % w/v |
|---|---|
| Baclofen | 0.100 |
| Methyl paraben NF | 0.150 |
| Propyl paraben NF | 0.020 |
| Sucralose NF | 0.025 |
| Natural grape flavor | 1.000 |
| Glycerin 99% USP | 10.000 |
| Purified water USP | 91.705 |

Example 3

A 2 mg/mL oral baclofen solution without a buffer having the formulation in Table 3 below was prepared by the procedure described in Example 1.

TABLE 3

| Ingredient | % w/v |
|---|---|
| Baclofen | 0.200 |
| Methyl paraben NF | 0.150 |
| Propyl paraben NF | 0.020 |
| Sucralose NF | 0.025 |
| Natural grape flavor | 1.000 |
| Glycerin 99% USP | 10.000 |
| Purified water USP | 91.605 |

Example 4

The following test method can be used to determine the amount of impurities, such as 4-(3-carboxymethyl)-3-hydroxy-2,5-dioxopyrrolidin-1-yl)-3-(4-chlorophenyl)butanoic acid, present in a baclofen oral solution. HPLC is performed using ion pair chromatography and two mobile phases, each containing acetic acid buffer (acetic acid and sodium acetate), methanol, and sodium 1-pentanesulfonate and differing in the concentration of acetic acid buffer and methanol. The column was a reverse phase C18 column.

One mobile phase is used until the peaks of interest have eluted. After, a gradient is created by mixing the first and second mobile phases. Several excipient peaks elute late into the run, and a gradient with a higher concentration of methanol in the mobile phase was added at the end of the run, to allow the final peaks to elute quicker.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended specification define the scope of the invention and that methods and structures within the scope of these specification and their equivalents be covered thereby.

All publications, patents and patent applications cited in this application are herein incorporated by reference to the same extent as if each individual publication, patent or patent application was specifically and individually indicated to be incorporated herein by reference.

What is claimed is:

1. A method of relaxing muscles or treating spasticity in a subject in need thereof comprising administering to the subject an effective amount of an aqueous oral solution comprising (i) baclofen, (ii) a buffer comprising citric acid, a salt of citric acid, or any combination thereof, and (iii) optionally one or more preservatives, wherein prior to the administration, the amount of 4-(3-carboxymethyl)-3-hydroxy-2,5-dioxopyrrolidin-1-yl)-3-(4-chlorophenyl)butanoic acid in the oral solution is determined to be below a threshold level and the oral solution is stored after the determination, but prior to the administration, at from about 2 to about 8° C.

2. The method of claim 1, wherein the threshold level is 0.2%.

* * * * *